US012680958B2

(12) United States Patent

Huang et al.

(10) Patent No.: US 12,680,958 B2

(45) Date of Patent: Jul. 14, 2026

(54) FLUORESCENCE IMMUNOASSAY DEVICE BASED ON INTEGRATION OF PHOTONIC CRYSTAL AND MAGNETIC BEADS

(71) Applicant: NATIONAL YANG MING CHIAO TUNG UNIVERSITY, Hsinchu City (TW)

(72) Inventors: Cheng-Sheng Huang, Hsinchu City (TW); Wen-Syang Hsu, Hsinchu City (TW); Lin-Yun Su, Taichung City (TW); Ying-Bin Wang, Yunlin County (TW); Yang Chen, New Taipei City (TW)

(73) Assignee: National Yang Ming Chiao Tung University, Hsinchu (TW)

( * ) Notice: Subject to any disclaimer, the term of this patent is extended or adjusted under 35 U.S.C. 154(b) by 1112 days.

(21) Appl. No.: 17/661,456

(22) Filed: Apr. 29, 2022

(65) Prior Publication Data

US 2022/0260490 A1 Aug. 18, 2022

Related U.S. Application Data

(62) Division of application No. 15/955,002, filed on Apr. 17, 2018, now Pat. No. 11,360,026.

(30) Foreign Application Priority Data

Jan. 31, 2018 (TW) ................................. 107103538

(51) Int. Cl.
G01N 21/64 (2006.01)
G01N 21/77 (2006.01)
(Continued)

(52) U.S. Cl.
CPC ....... G01N 21/6428 (2013.01); G01N 21/648 (2013.01); G01N 21/7743 (2013.01);
(Continued)

(58) Field of Classification Search
CPC ........... G01N 21/6428; G01N 21/7743; G01N 33/582; G01N 33/54326; G01N 21/648;
(Continued)

(56) References Cited

U.S. PATENT DOCUMENTS 5,738,825 A * 4/1998 Rudigier .............. G01N 21/253
422/82.11
5,822,472 A * 10/1998 Danielzik .......... G01N 21/7703
385/12
(Continued)

FOREIGN PATENT DOCUMENTS

| CN | 101846674 | * | 9/2010 | |
| EP | 0465577 B1 | * | 3/1994 | ........... G01N 33/532 |
| TW | 201432246 | * | 8/2014 | |

OTHER PUBLICATIONS

Tabakman et al, "Plasmonic Substrates for Multiplexed Protein Microarrays with Femtomolar Sensitivity and Broad Dynamic Range"; NIH Public Access, PNC Jul. 23, 2012. (Year: 2012).*

(Continued)

*Primary Examiner* — Christopher L Chin
(74) *Attorney, Agent, or Firm* — Rosenberg, Klein & Lee

(57) ABSTRACT

A fluorescence immunoassay device based on integration of a photonic crystal and magnetic beads and a method thereof are provided. Magnetic beads with high surface-to-volume ratio are used as carriers of fluorescent molecules to obtain higher fluorescence density. The electric field on the surface of the photonic crystal is enhanced through excitation of photonic crystal resonance. The intensity of the fluorescence signal excited by the enhanced electric field is increased. Moreover, through interaction with the photonic crystal, some fluorescent signals that originally cannot be received by the fluorescent sensor are coupled to the photonic crystal resonant modes and reradiate toward the fluorescent sensor, thereby increasing collection efficiency. The fluorescence (Continued)

signals generated by fluorescent molecules on the magnetic beads are significantly intensified, which could lower the detection limit. Furthermore, the magnetic beads aggregation method can achieve the detection capability that cannot be achieved by the current fluorescent immunoassay.

9 Claims, 10 Drawing Sheets

(51) Int. Cl.
     *G01N 33/543*        (2006.01)
     *G01N 33/58*         (2006.01)
(52) U.S. Cl.
     CPC . *G01N 33/54326* (2013.01); *G01N 33/54373* (2013.01); *G01N 33/582* (2013.01); *G01N 2021/6439* (2013.01); *G01N 2021/7786* (2013.01)
(58) Field of Classification Search
     CPC ..... G01N 33/54373; G01N 2021/7786; G01N 2021/6439; G01N 33/54346
     USPC ......... 422/82.08, 82.11; 435/288.7; 436/164, 436/172, 524, 526, 527, 805
     See application file for complete search history.

(56) References Cited

U.S. PATENT DOCUMENTS

| | | | |
|---|---|---|---|
| 6,921,642 B2 * | 7/2005 | Kingsmore ......... | C12Q 1/6804 435/6.12 |
| 7,768,640 B2 * | 8/2010 | Cunningham ....... | G01N 21/648 356/417 |
| 7,820,106 B2 * | 10/2010 | Budach .............. | G01N 21/7743 422/82.11 |

OTHER PUBLICATIONS

Mathias et al, "Improved Sensitivity of DNA Microarrays Using Photonic Crystal Enhanced Fluorescence", Department of Bioengineering, PMC 2010, Aug. 2016; Anal. Chem, Aug. 15, 2010; 82(16), 6854-6860. (Year: 2010).*
Patrick C. Mathias, Nikhil Ganesh, Brian T. Cunningham, Application of Photonic Crystal Enhanced Fluorescence to a Cytokine Immunoassay; Analytical Chemistry, vol. 80, No. 23, Dec. 1, 2008, pp. 9013-9021. (Year: 2008).*
Nikhil Ganesh, Ian D. Block, Patrick C. Mathias, Wei Zhang, Edmond Chow, Viktor Malyarchuk, Brian T. Cunningham; Leaky-Mode Assisted Fluorescence Extraction: Application to Fluorescence Enhancement Biosensors; Dec. 22, 2008/vol. 16, No. 26/Optics Express 21626. (Year: 2008).*
M. Celebre, C. Domenici, R. Francesconi, A. Ahluwalla, A. Schirone; A Comparative Study of Efficiencies of Fibre Optic and Prism TIRF Sensors; Meas. Sci. Technol. 3 (1992) 1166-1173, Printed in the UK. (Year: 1992).*
Cheng-Yeh Huang, Po-Huai Shih, Po-Yen Tsai, I-Chin Lee, Hsin-Yun Hsu, Hong-Yuan Huang, Shih- Kang Fan, and Wensyang Hsu; AMPFLUID: Aggregation Magnified Post-Assay Fluorescence for Ultrasensitive Immunodetection on Digital Microfluidies; No. 103, No. 2, Feb. 2015, Proceedings of the IEEE. (Year: 2015).*
Gennilyn Joy Bilbes Lacuesta, "Detectingg Ricin Using an Immunoassay on Magnetic Nanoparticles on a Photonic Crystal", ProQuest No. 10252743 (2017), pp. 1-32, (Year: 2017).*
Office Action issued on Dec. 29, 2020 for corresponding CN application No. 201810190999.9 (Year: 2020).*

* cited by examiner

12

151

12

151 magnetic force magnetic
device

27

FLUORESCENCE IMMUNOASSAY DEVICE BASED ON INTEGRATION OF PHOTONIC CRYSTAL AND MAGNETIC BEADS

This application is a division of U.S. patent application Ser. No. 15/955,002 filed on Apr. 17, 2018 which claims priority for Taiwan patent application no. 107103538 filed on Jan. 31, 2018, the content of which is incorporated by reference in its entirety.

BACKGROUND OF THE INVENTION

Field of the Invention

The present invention relates to a fluorescence immuno-assay technology, particularly to a fluorescence immunoas-say device based on the integration of a photonic crystal and magnetic beads.

Description of the Related Art

The technology using fluorescence to detect the concen-tration of a tested object (such as protein or DNA) is one of the most common methods in modern laboratories. Among them, the immunofluorescence method is a frequently-seen method using antibodies to detect antigens and measure concentrations. In the immunofluorescence method, a cap-ture antibody bonds with an antigen specifically; a detection antibody containing labelling fluorescence bonds with the antigen; a light source is used to excite fluorescence; a sensor detects the intensity of the fluorescence signal and determines the concentration of the antigen.

Although the immunofluorescence method has high sen-sitivity, the detection limit thereof is still insufficient. There-fore, the application of the immunofluorescence method is often limited. For example, in measuring a tested object having a low concentration, the intensity of fluorescence signal is too low to be precisely detected and analyzed. Therefore, the conventional immunofluorescence method is hard to measure low-concentration tested objects. While the volume of the tested object is too small, the detection limit would impair using dilution to increase the volume of the tested object. In such case, the number of samples will be too small to acquire reliable results.

The following two methods are often used to lower the detection limit, including the method using an optical method to increase the intensity of the fluorescence signals and the method increasing the surface-to-volume ratio of the biological carrier to increase the density of the fluorescence signals.

1. The method using an optical waveguide element and a surface plasma resonance (SPR) element: these ele-ments induce light resonance to increase the intensity of the fluorescence signals on planar carriers (such as glass plates or well plates). These elements can increase the signal intensity to several times that of the ordinary immunofluorescence method. However, the intensity of increased fluorescence signals is insufficient to signifi-cantly lower the detection limit.

2. The method increasing the surface-to-volume ratio to increase the density of fluorescence signals: the glass plate and well plate are common planar biological carriers. Their limited surface-to-volume ratio leads to a detection limit of about 10-50 pg/ml. Magnetic beads and nanorods are used to increase the surface-to-vol-ume ratio and increase the density of fluorescence signals. The method can increase the intensity of fluorescence signals several times and lower the detection limit. However, the times of increasing intensity is insufficient to significantly lower the detection limit.

SUMMARY OF THE INVENTION

The primary objective of the present invention is to provide a fluorescence immunoassay device based on the integration of a photonic crystal and magnetic beads and a fluorescence immunoassay method using the same, wherein the optical characteristics of the photonic crystal and the magnetic beads functioning as the carriers of fluorescent molecules are used to effectively increase the fluorescence signal intensity and lower the detection limit, whereby to overcome the problems of the conventional technology.

Another objective of the present invention is to provide a fluorescence immunoassay device based on the integration of a photonic crystal and magnetic beads and a fluorescence immunoassay method using the same, which use the char-acteristic aggregation behavior of the magnetic beads to further increase the intensity of fluorescence signals and lower the detection limit.

In order to achieve the abovementioned objectives, the present invention proposes a fluorescence immunoassay device based on the integration of a photonic crystal and magnetic beads, which comprises a photonic crystal, at least one magnetic bead, a light source and a fluorescence detec-tor. Several fluorescent molecules are bonded to the surface of a magnetic bead, and the magnetic bead is between a substrate and the surface of the photonic crystal. A tested biological molecule is bonded to the surface of each mag-netic bead. Owing to the optical characteristics of the photonic crystal, the photonic crystal resonates with the incident exciting light provided by the light source, whereby to enhance the electric filed on the surface. The electric field excites the fluorescent molecules to generate fluorescence signals intensified by the electric field. The fluorescence detector receives the fluorescence signals emitted by the fluorescent molecules and the fluorescence signals reflected by the surface of the photonic crystal and processes the fluorescence signals to form a sensed image.

In one embodiment, the tested biological molecules has a concentration of at least $10^{-3}$ pg/ml.

In one embodiment, the tested biological molecule is a material that can be detected by the fluorescence immuno-assay method, such as a nucleic acid, an antigen, an anti-body, a binding protein, phytohematoagglutinin, a hormone receptor, or a small-molecule compound.

In one embodiment, the fluorescence immunoassay device of the present invention comprises a plurality of magnetic beads; the device of the present invention further comprises a magnetic device disposed near the magnetic beads and used to concentrate the magnetic beads on the surface of the photonic crystal. In this embodiment, the tested biological molecules have a concentration of at least $10^{-4}$ pg/ml.

In one embodiment, the photonic crystal is a resonant waveguide grating structure. The resonant waveguide grat-ing structure includes a substrate, a grating layer and a waveguide layer. The present invention does not particularly limit the relative positions of the components of the resonant waveguide grating structure as long as the mode of the waveguide layer can overlap the grating layer.

In one embodiment, the fluorescence detector detects a plurality of pixels of the sensed image and sets the pixels whose pixel values are smaller than a black balance value to be zero, whereby to eliminate the noise in the sensed image.

In one embodiment, the fluorescence immunoassay device of the present invention further comprises an image processor. The image processor receives the sensed image and analyzes the intensity of the fluorescence signal according to the sensed image.

The present invention also proposes a fluorescence immunoassay method based on the integration of a photonic crystal and magnetic beads, which comprises steps: providing at least one magnetic bead; bonding a plurality of fluorescent molecules to the surface of the magnetic bead, wherein a tested biological molecule is bonded to each fluorescent molecule; disposing the magnetic bead on the surface of a photonic crystal; providing an incident exciting light; the exciting light cooperating with the surface electric field of the photonic crystal to excite the fluorescent molecules to generate fluorescence signals intensified by the electric field; receiving the fluorescence signals, which are emitted to the fluorescence detector by the fluorescent molecules and reflected by the surface of the photonic crystal; and processing the fluorescence signals into a sensed image.

In one embodiment, the method of the present invention further comprises steps: setting a black balance value; determining whether the pixel value of each of the plurality of pixels of the sensed image is smaller than the black balance value; and setting the pixels whose pixel values are smaller than the black balance value to be zero, whereby to eliminate the noise of the sensed image.

In one embodiment, the method of the present invention further comprises steps: receiving the sensed image; and analyzing the intensities of the fluorescence signals according to the sensed image.

Different from the conventional technology using the optical waveguide element or the surface plasma resonant element to enhance fluorescence, or the conventional technology using the magnetic beads/nanorods as the biological carriers to lower the detection limit, the present invention uses the guided-mode resonance of the photonic crystal to enhance the excitement of fluorescence signals; the present invention further directs the dispersive fluorescence signals to the fluorescence detector to intensify the fluorescence signals; the present invention also uses the high surface-to-volume characteristic of the magnetic beads to achieve further higher intensity and density of fluorescence signals; the present invention also uses the aggregation of magnetic beads to significantly intensify the fluorescence signals.

Below, embodiments are described in detail to make easily understood the objectives, technical contents, characteristics and accomplishments of the present invention.

BRIEF DESCRIPTION OF THE DRAWINGS

FIG. 5A and FIG. 5B are diagrams schematically showing the statuses before and after magnetic bead aggregation according to one embodiment of the present invention, wherein FIG. 5A shows the status before magnetic bead aggregation and FIG. 5B shows the status after magnetic bead aggregation;

FIG. 8A and FIG. 8B are diagrams showing the average fluorescent intensity of each magnetic bead and the concentration of the antigen, wherein FIG. 8A shows the experimental results of the control group and FIG. 8B shows the results of the experimental group (using the photonic crystal), and wherein ● denotes the experimental data obtained after magnetic bead aggregation and X denotes the experimental data obtained before magnetic bead aggregation.

DETAILED DESCRIPTION OF THE INVENTION

Figure 1:
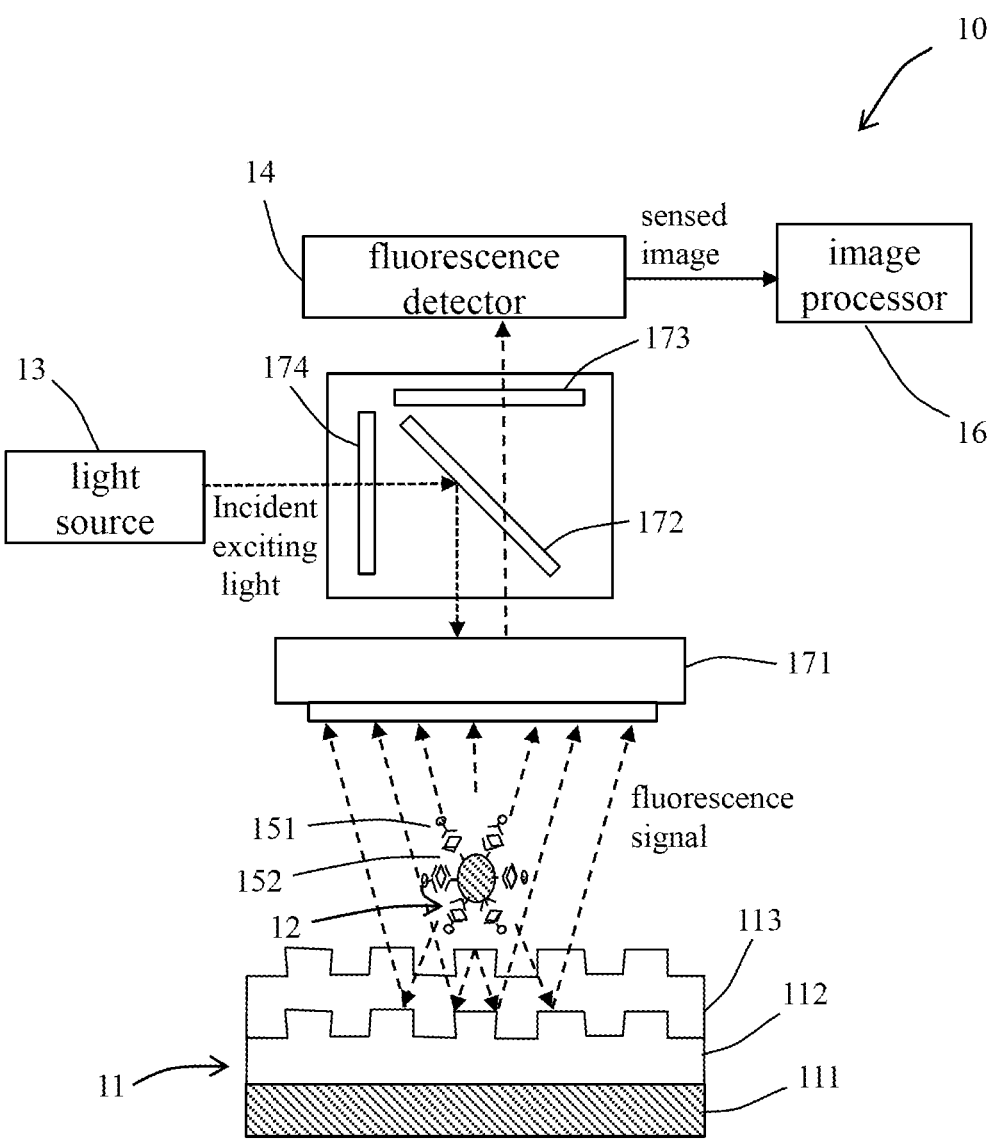
FIG. 1 is a diagram schematically showing a fluorescence immunoassay device based on the integration of a photonic crystal and magnetic beads according to a first embodiment of the present invention.

Refer to FIG. 1. According to a first embodiment of the present invention, the fluorescence immunoassay device 10 based on the integration of a photonic crystal and magnetic beads comprises a photonic crystal (PC) 11, at least one magnetic bead 12, a light source 13 and a fluorescence detector 14. A plurality of fluorescent molecules 151 is bonded to the surface of the magnetic bead 12, and the fluorescent molecules 151 are combined with tested biological molecules 152. The biological molecule 152 may be selected from a group including nucleic acids, antigens, antibodies, binding proteins, phytohematoagglutinin, hormone receptors, and small-molecule compounds. The magnetic bead 12 is disposed on the surface of the photonic crystal 11. The light source 13 provides an incident exciting light. The incident exciting light resonates with the photonic crystal 11 to intensify the electric field on the surface of the photonic crystal 11. The intensified electric field excites enhanced fluorescence signals from the fluorescent molecules 151. The fluorescence detector 14 receives the fluorescence signals emitted by the fluorescent molecules 151. The fluorescence signal projected to the photonic crystal 11 is also directed to the fluorescence detector 14. Thereby, the fluorescence detector 14 receives more fluorescence signals, which can be processed into a sensed image.

In the first embodiment, an object lens 171 projects the incident exciting light provided by the light source 13 to the fluorescent molecules 151 and receives the fluorescence signals emitted by the fluorescent molecules 151. A light splitter 172 distributes the incident exciting light and the received fluorescence signals to two different optical paths, and two filters 173 and 174 are used to decrease the mutual interference.

In the first embodiment, a black balance calibration is performed on the sensed image detected by the fluorescence detector 14 to eliminate the noise in the sensed image. In the black balance calibration, the fluorescence detector 14 detects the pixel values of a plurality of pixels of the sensed image; a black balance value is set; the pixel whose pixel value is smaller than the black balance value is set to be zero. Thereby, the noise in the sensed image is eliminated. Then, an image processor 16 receives the sensed image and analyzes the intensities of the fluorescence signals on the magnetic beads 12 according to the sensed image.

Figure 2:
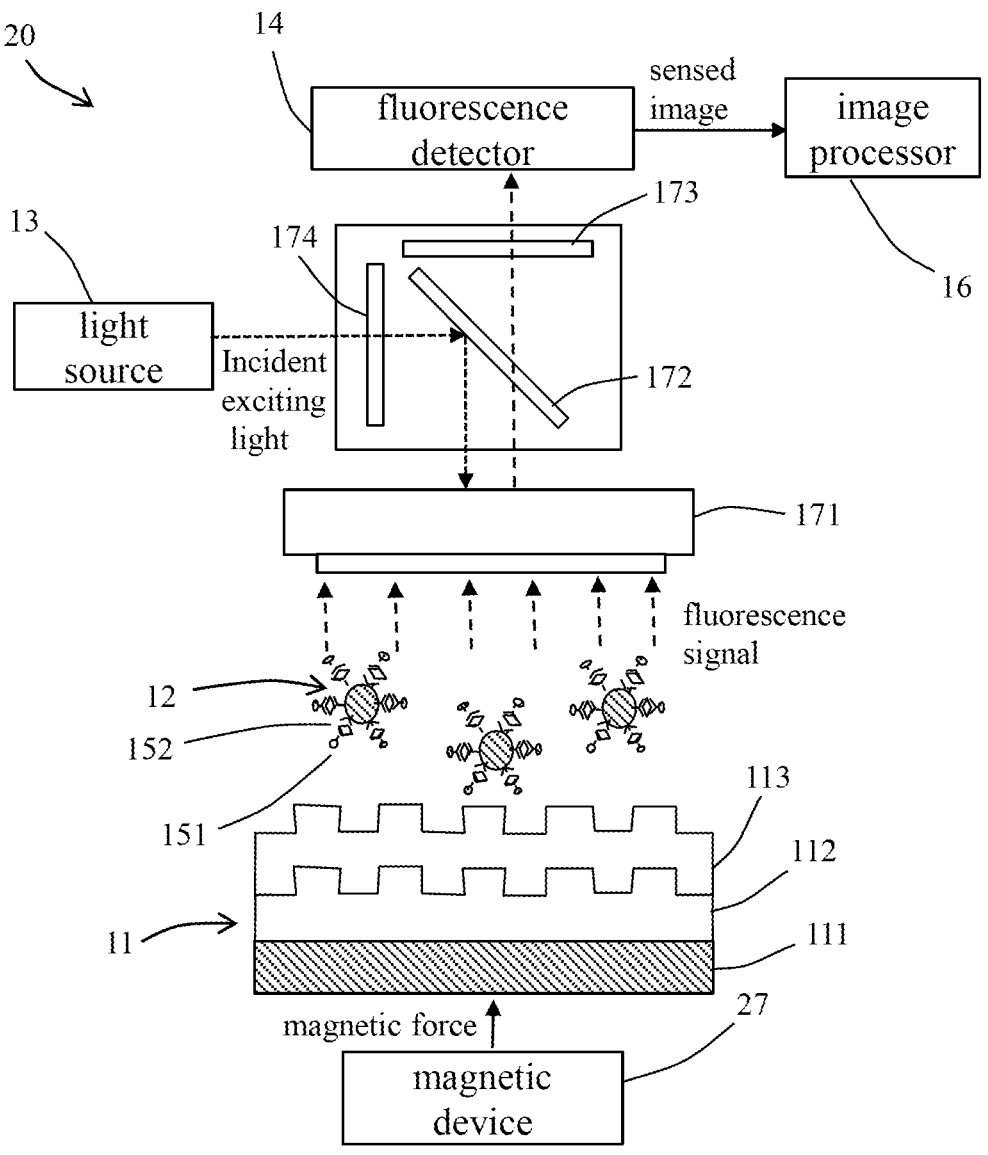
FIG. 2 is a diagram schematically showing a fluorescence immunoassay device based on the integration of a photonic crystal and magnetic beads according to a second embodiment of the present invention.

Refer to FIG. 2. The structure of the fluorescence immunoassay device 20 based on the integration of a photonic crystal and magnetic beads of a second embodiment is essentially similar to that of the first embodiment but is different from that of the first embodiment in that the device uses a plurality of magnetic beads 12 and that a magnetic device 27, such as a magnet, is disposed near the magnetic beads 12. The magnetic force of the magnetic device 27 will aggregate the magnetic beads 12 on the surface of the photonic crystal 11. The rest of the second embodiment is the same as that of the first embodiment and will not repeat herein.

In the present invention, the photonic crystal 11 may be a guided-mode resonance (GMR) grating structure or a resonance waveguide grating (RWG) structure. As shown in FIG. 1, the guided-mode resonance (GMR) grating structure of the photonic crystal 11 includes a substrate 111, a low-refractive index grating layer 112 formed on the substrate 111, and a high-refractive index waveguide layer 113 formed on the grating layer 112. The substrate 111 may be made of a silicon chip, a glass material, or a polymer material. The low-refractive index grating layer 112 may be made of silica. The high-refractive index waveguide layer 113 may be made of an organic material or an inorganic material, such as titanium dioxide ($TiO_2$), tantalum pentoxide ($Ta_2O_5$), zinc peroxide ($ZnO_2$), hafnium oxide ($HfO_2$), or niobium pentoxide ($Nb_2O_5$). In one embodiment, the substrate 111 of the guided-mode resonance (GMR) grating structure of the photonic crystal 11 is made of polyethylene terephthalate (PET); a UV-curable resin (Noaland 68) is formed the substrate 111 to have a grating structure (not shown in the drawings); the silica-based grating layer 112 and the titanium dioxide-based waveguide layer 113, which respectively have appropriate thicknesses, are coated on the UV-set resin. The structure of the photonic crystal 11 disclosed in the above embodiment are only to exemplify the photonic crystal 11 but not to limit the scope of the present invention. The present invention does not particularly limit the relative positions of the components of the photonic crystal 11 as long as the mode of the waveguide layer 113 can overlap the grating layer 112.

In the present invention, the dimensional design of the photonic crystal 11 includes the designs of the period of the grating, the depth of the grating, the duty cycle of the grating, and the thickness of the high-refractive index layer. At the same time, appropriate materials are adopted to realize the high-refractive index layer and the low-refractive index layer. Thereby, the photonic crystal 11 can couple the external light to the mode of the structure to induce the resonance of the structure.

Below are described in detail the optical characteristics of the photonic crystal and the principles that the photonic crystal intensifies the fluorescence. The optical characteristics of the photonic crystal include a far-field effect and a near-field effect of the photonic crystal.

I. Far-Field Effect of Photonic Crystal

The resonance of light and a waveguide is called the guided-mode resonance (GMR) effect. The phase match of an incident light and the guided mode of the waveguide will take place while the incident light is at a specified angle and with a specified wavelength. The light with the specified wavelength is coupled into the waveguide layer and propagated therein. However, the existence of a grating makes the light wave unable to always propagate along the waveguide layer but be diffracted out of the waveguide layer to form a leaky mode. The coupled-out light will be split to lights in two different directions, which will respectively have different interferences with the zero-order diffraction light. The light in the reflection direct and the reflected zero-order diffraction light generates a complete constructive interference; i.e. the reflectivity is 100%. The light in the transmission direct and the transmitting zero-order diffraction light generates a complete destructive interference; i.e. no light can transmit. Such a phenomenon can be observed in the transmission spectrum and the reflection spectrum. While a wideband light is vertically incident to a photonic crystal having an appropriate dimensional design and using an appropriate material, the light having a specified wavelength will resonate with the structure and reflect from the photonic crystal. The rest of the wideband light will transmit through the photonic crystal. Thus, a spectrum with a peak can be seen in the reflection spectrum, and a spectrum with a dip can be seen in the transmission spectrum.

II. Near-Field Effect of Photonic Crystal

As mentioned above, while the light at a specified angle and with a specified wavelength is coupled to the resonant mode of the structure, the specified wavelength is called the resonant wavelength, and the specified angle is called the resonant angle. The energy carried by the light waves is concentrated to propagate in the waveguide layer. The evanescent wave generated thereby will extend to the surface of the structure and obviously intensify the electric field on the surface of the photonic crystal. The energy level transition induces the fluorescent molecules to generate light. While an electric field is applied, the fluorescent molecules are excited to an excited state. While returning to the ground state, the fluorescent molecules release photons and generate fluorescence signals. If the strength of the electric field increases, the excited fluorescent molecules and the released energy also increase. Therefore, the number of the excited fluorescent molecules and the amount of the released energy positively correlates with the strength of the electric field. Simulations are undertaken for the distributions of the electric fields on the surface of the photonic crystal in the resonant mode and the non-resonant mode. From the results of the simulations, it is learned: while the photonic crystal is excited to resonance, the surface electric field thereof is intensified hundreds of times; while the photonic crystal is in a non-resonant state, the surface electric field thereof does not increase.

III. Principles of Intensifying Fluorescence

Figure 3A:
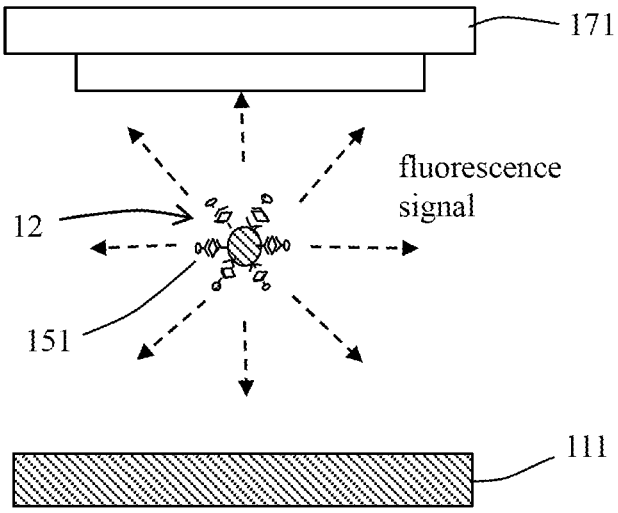
FIG. 3A and FIG. 3B are diagrams schematically showing extraction mechanisms according to embodiments of the present invention, wherein the embodiment shown in FIG. 3A is free of the photonic crystal and the embodiment shown in FIG. 3B uses the photonic crystal.
Figure 3B:
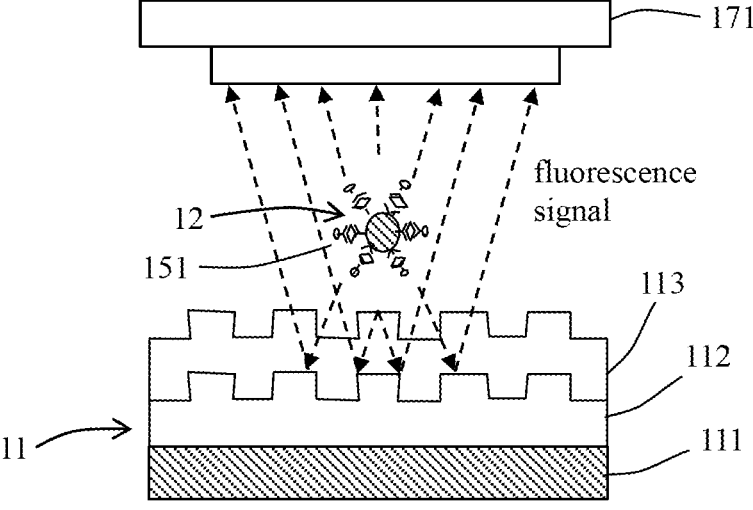

There are two principles that the photonic crystal intensifies fluorescence signals: one is the enhanced excitation principle, and the other is the enhanced extraction principle. About the enhanced excitation principle, the evanescent wave, which has been introduced in the description of the near-field effect, can increase the strength of the surface electric field to increase the number of the excited fluorescent molecules and the amount of the released energy. Refer to FIG. 3A and FIG. 3B for the introduction of the enhanced extraction principle. As shown in FIG. 3A, while there is no photonic crystal 11, no interaction between the fluorescence signal and the substrate 111 will take place. A minor amount of light will be detected by the fluorescence detector (omitted in the drawing) through the Fresnel reflection. However, most of the light is radiated to all directions. As shown in FIG. 3B, while there is a photonic crystal 11, a portion of the fluorescence signals, which are projected to the photonic crystal 11 and meet the coupling condition of the photonic crystal 11, are coupled to the resonant mode of the photonic crystal 11. Then, the light is coupled out and directed to the fluorescence detector 14. Thereby, the fluorescence detector 14 can receive more fluorescence signals. Thus is enhanced the extraction of fluorescence signals.

Below are described in detail the intensity variations of fluorescence signals observed in the fluorescence intensification experiments used to support the practicability of the present invention.

I. Methods for Fluorescence Intensification Experiments

Figure 4:
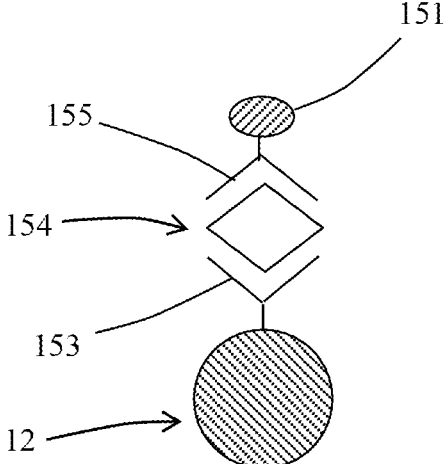
FIG. 4 is a diagram schematically showing that a fluorescent molecule is bonded to a magnetic bead according to one embodiment of the present invention.

Refer to FIG. 4. The antigen 154 is used to exemplify the tested biological molecule. The steps of bonding the fluorescent molecules to the magnetic beads include 1. Mixing the magnetic beads 12, which have been modified with capture antibodies 153, with the antigens 154 uniformly to bond the capture antibody-modified magnetic beads 12 to the antigens 154;

2. Removing the residual antigens 154, which are not bonded to the magnetic beads 12, through flushing to form a first product;

3. Adding detection antibodies 155 to the solution of the first product, mixing them uniformly, and removing the residual detection antibodies 155, which are not bonded to the first product, through flushing to form a second product;

4. Adding the fluorescent molecules 151 to the solution of the second product, mixing them uniformly, removing the residual fluorescent molecules 151, which are not bonded to the second product, through flushing to form a third product; and 5. After the flushing in the abovementioned step is completed, preserving the magnetic beads 12 in a buffer solution for the succeeding measurements.

The black balance calibration of the microscope is introduced below. Because of the environment, the measuring elements and the measuring circuit, the fluorescence signals detected by the fluorescent microscope have a given amount of noise. Theoretically, the background or magnetic beads free of fluorescent molecules should not generate fluorescence signals while there is no illumination of a mercury lamp. However, the CCD light detection element can still detect signals in such case. In order to exempt the experimental results from being affected by the environment and the electronic noise, a black balance value is set for the fluorescent microscope. While the detected value of a pixel is smaller than the black balance value, the fluorescent microscope sets the detected value to be zero, whereby to eliminate the interference from the environmental light sources.

Figure 5A:
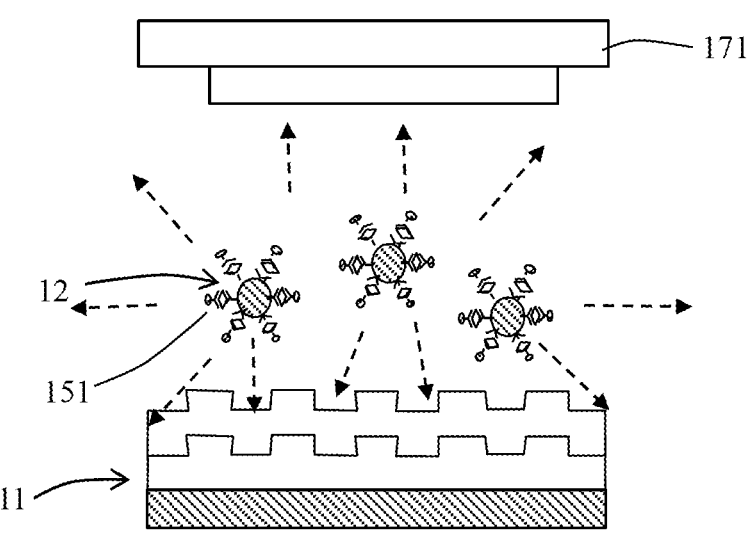
Figure 5B:
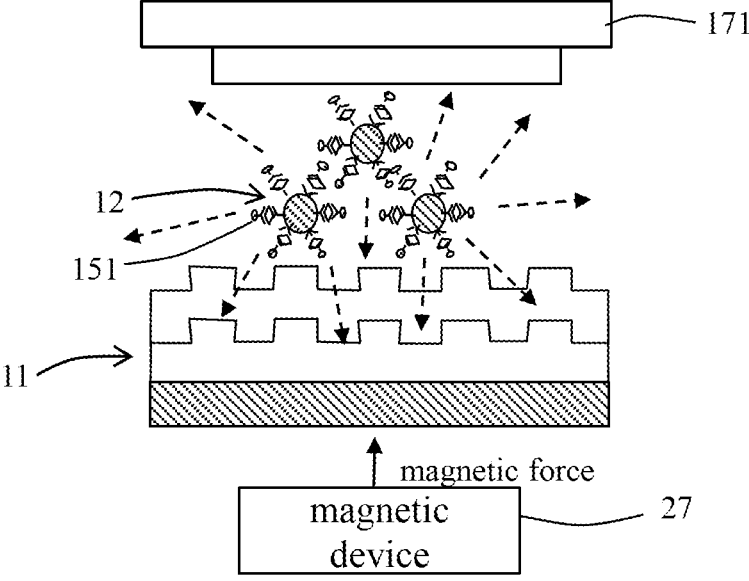
Figure 6A:
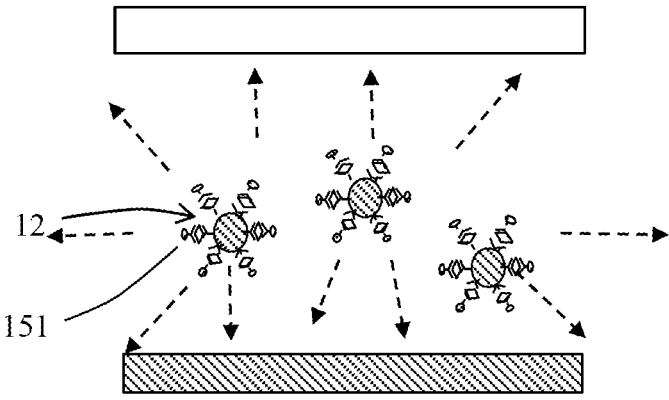
FIGS. 6A-6D are diagrams schematically showing a subgroup where magnetic beads are not aggregated in the control group, a subgroup where magnetic beads are aggregated in the control group, a subgroup where magnetic beads are not aggregated in the experimental group (using the photonic crystal) and a subgroup where magnetic beads are aggregated in the experimental group in sequence.
Figure 6B:
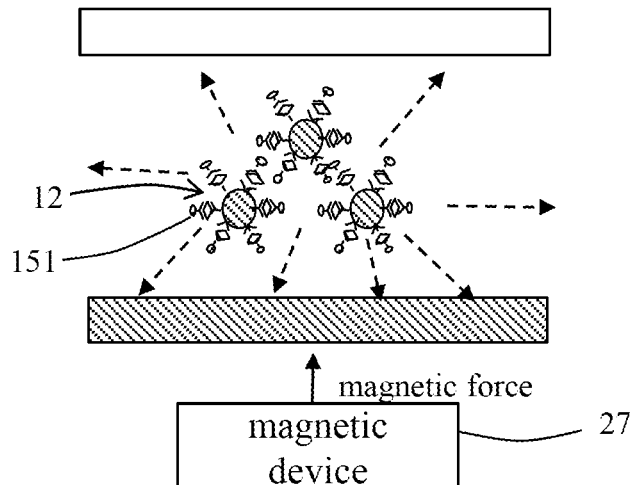
Figure 6C:
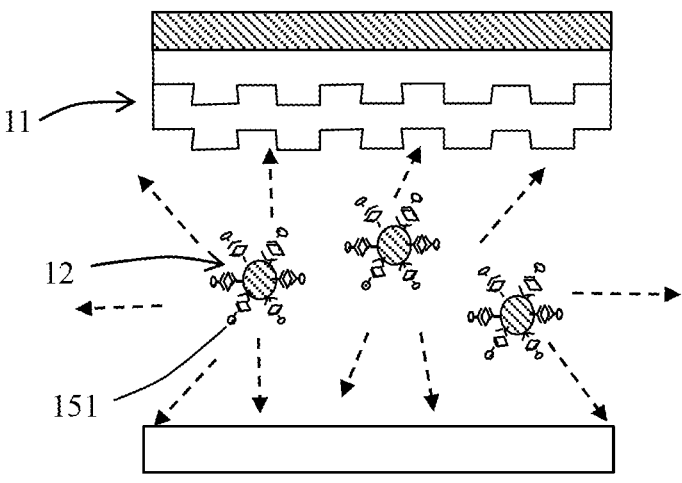
Figure 6D:
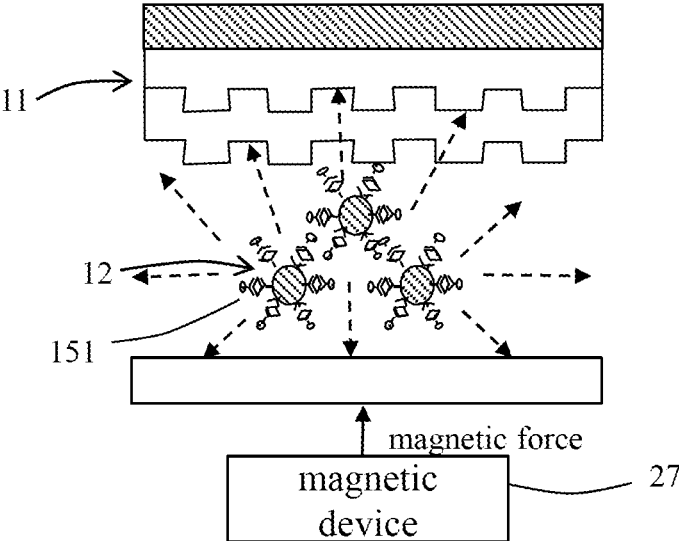

Refer to FIG. 5A and FIG. 5B diagrams schematically showing the distributions of the magnetic beads before and after using a magnetic device. As shown in the diagrams, the magnetic force of the magnetic device 27 can gather together the magnetic beads 12, which are originally dispersed. The succeeding experiments will prove that the fluorescent molecules 151 of the aggregated magnetic beads 12 can effectively enhance the intensity of the fluorescence emitted by the fluorescent molecules 151. The residual magnetic flux density (br) is about 14.2-14.8 KGs. The maximum magnetic energy product (BHmax) is about 49-53

MGOe. However, the present invention does not particularly limit the magnetic force of the magnetic device 27 as long as the magnetic force of the magnetic device 27 is sufficient to gather together the magnetic beads 12.

In order to prove that both the aggregation of the magnetic beads and the utilization of the photonic crystal are effective in enhancing fluorescence, the experiment includes a control group free of the photonic crystal 11 and an experimental group using the photonic crystal 11. The fluorescence intensity difference of the two groups is measured. Also is measured the fluorescence intensity difference of the subgroup where the magnetic beads are aggregated and the subgroup where the magnetic beads are not aggregated in each of the control group and the experimental group. Refer to FIGS. 6A-6D diagrams respectively schematically showing the subgroup where the magnetic beads are not aggregated of the control group, the subgroup where the magnetic beads are aggregated of the control group, the subgroup where the magnetic beads are not aggregated of the experimental group, and the subgroup where the magnetic beads are aggregated of the experimental group.

In the experiments, the steps to measure fluorescence signals include

1. Adjusting the black balance value to let the intensity of the magnetic bead-free portion be regarded as zero so as to eliminate the interference of the noise;

2. Aspiring the sample where the fluorescent molecules have been bonded, applying the sample on the surface of a piece of glass, and using a magnet to aggregate the magnetic beads (if the sample belongs to the subgroup where the magnetic beads are aggregated);

3. Using a fluorescent microscope in cooperation with a mercury lamp or a fluorescence scanner to excite the fluorescent molecules, and taking pictures; and 4. Using an image analysis software to obtain the brightness of each magnetic bead.

II. Analysis of Results

Figure 7:
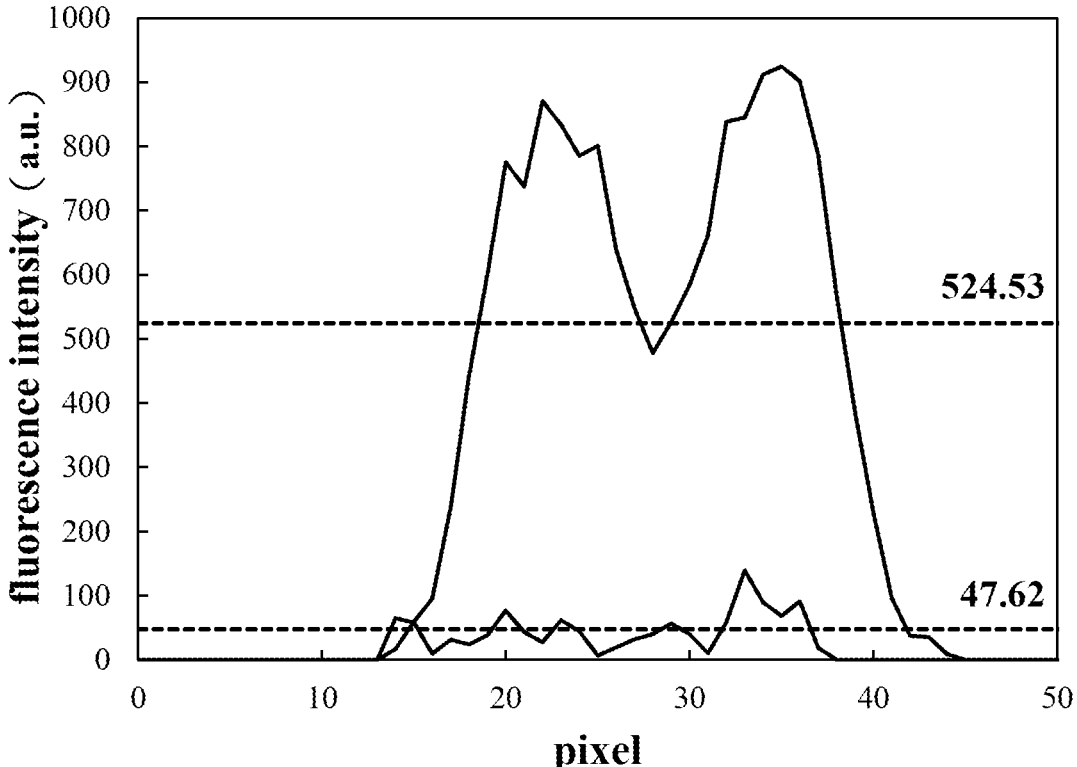
FIG. 7 is a diagram showing the fluorescence signals from a single magnetic bead in a control group (free of the photonic crystal) and an experimental group (using the photonic crystal), wherein the results of the experimental group and the control group are respectively represented by the upper curve and the lower curve, and wherein the dashed-lines represents the average values.

1) Comparison of the fluorescence intensities of the control group and experimental group both using a single magnetic bead The phenomenon that the photonic crystal can intensify fluorescence signals has been proved by many persons. All the conventional technologies use the photonic crystal as a substrate and directly perform immunoassay on the substrate. It has not yet been tried before: the photonic crystal is used to enhance the intensity of fluorescence signals in a magnetic bead-based immunoassay process. In the analysis of a single magnetic bead, the area of each magnetic bead is about 20×20 pixels in the case that the concentration of the tested biological molecules is 1000 pg/ml. The images of the magnetic beads in the control group and the experimental group are measured with an image analysis software to observe the variation of the intensity of each pixel. As shown in FIG. 7, the average intensity of the control group is 47.62a.u.; the average intensity of the experimental group is 524.53a.u. Therefore, the intensity is increased by about 11 times. The fluorescence signals of some pixels in the control group are undetectable. However, the fluorescence signals of the same pixels in the experimental group can be detected. Therefore, the photonic crystal can enhance the fluorescence signals on the surface of a single magnetic bead.

Figure 8A:
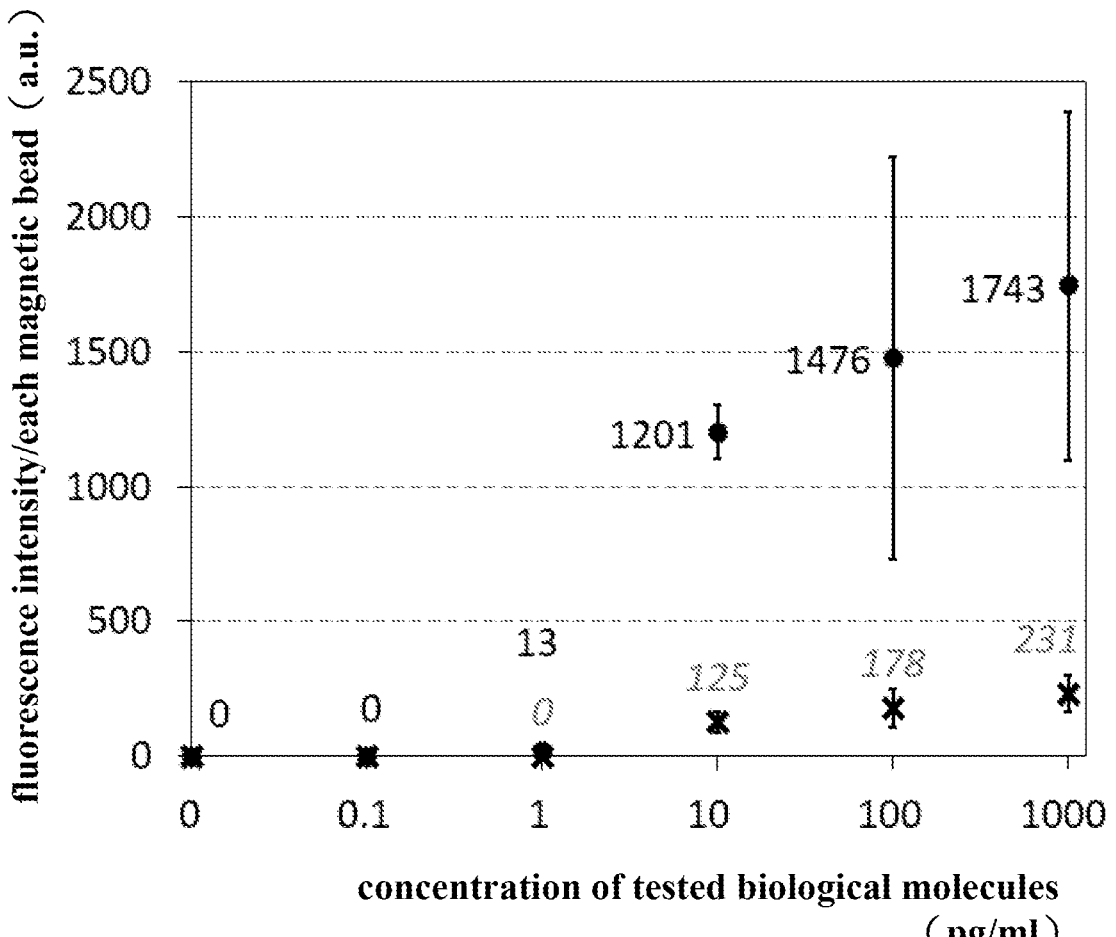
Figure 8B:
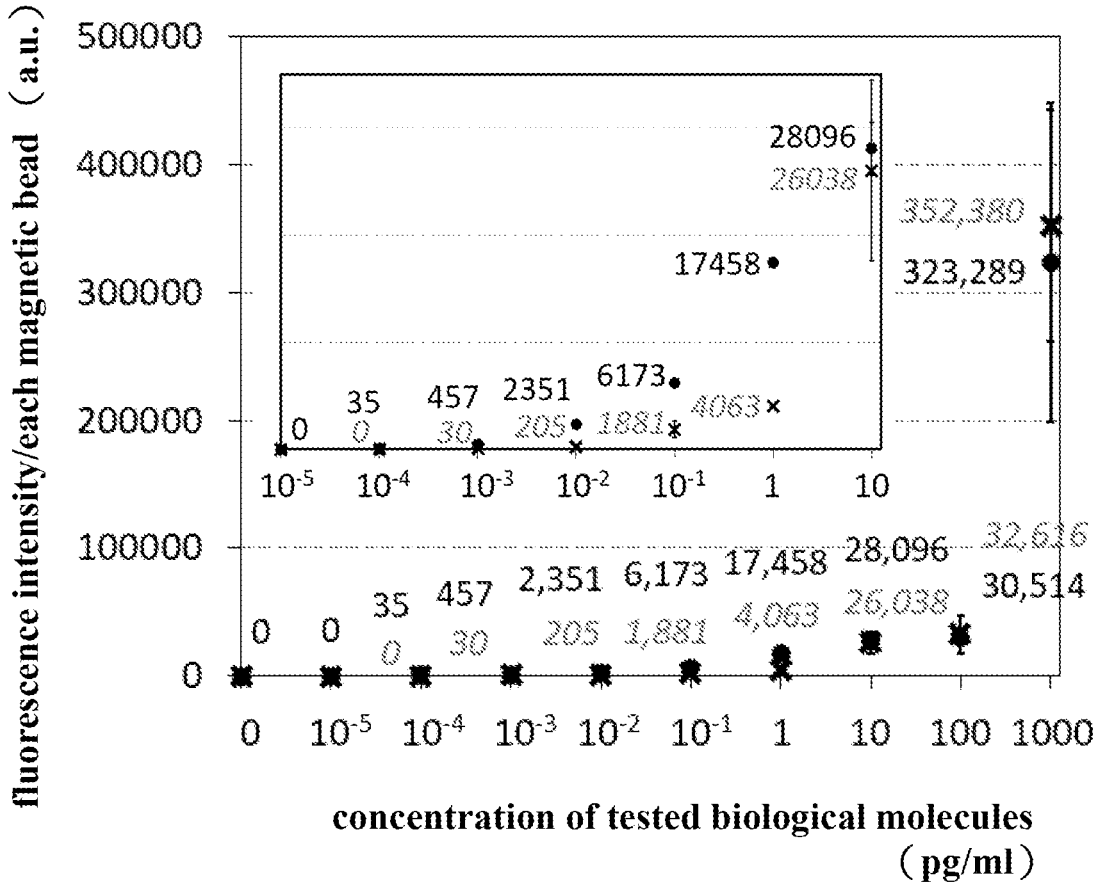

2) Comparison of the fluorescence intensities at different concentrations of the control group and experimental group both using a plurality of magnetic beads FIG. 8A and FIG. 8B respectively shows the relationships between the average brightness of each magnetic bead and the concentrations of the antigens in the control group and the experimental group. As shown in FIG. 8A, while the concentration of the tested biological molecules is 100 pg/ml, the intensities of the fluorescence signals in the subgroup where the magnetic beads are not aggregated of the control group and the subgroup where the magnetic beads are aggregated of the control group are respectively 178a.u. and 1476a.u. Therefore, the intensity is increased by over 8 times. In the subgroup where the magnetic beads are not aggregated of the control group, the lowest concentration of the tested biological molecules, which can be detected, is 10 pg/ml. In the subgroup where the magnetic beads are aggregated of the control group, the lowest concentration of the tested biological molecules, which can be detected, is 1 pg/ml. Therefore, the aggregation of magnetic beads can lower the detection limit by an order of magnitude in the control group. Thus is proved that the aggregation of magnetic beads can intensify fluorescence in the control group.

As shown in FIG. 8B, in the subgroup where the magnetic beads are not aggregated of the experimental group, the lowest concentration of the tested biological molecules, which can be detected, is $10^{-3}$ pg/ml; in the subgroup where the magnetic beads are aggregated of the experimental group, the lowest concentration of the tested biological molecules, which can be detected, is $10^{-4}$ pg/ml. Therefore, the aggregation of magnetic beads can also lower the detection limit by an order of magnitude in the experimental group. Thus is proved that the aggregation of magnetic beads can also intensify fluorescence in the experimental group.

In comparing FIG. 8A and FIG. 8B, it is learned: while the concentration of the tested biological molecules is 1 pg/ml, the intensity of the fluorescence signals in the subgroup where the magnetic beads are aggregated in the control group is 13 a.u.; at the same concentration of the tested biological molecules, the intensity of the fluorescence signals in the subgroup where the magnetic beads are aggregated in the experimental group is 17458 a.u. Therefore, the intensity of fluorescence signals is increased by over 1300 times from the control group to the experiment group in the case that the concentration of the tested biological molecules is 1 pg/ml and the magnetic beads are aggregated. While the concentration of the tested biological molecules is $10^{-1}$ pg/ml, the intensity of the fluorescence signals of the control group is decreased to 0 a.u. no matter whether the magnetic beads are aggregated or not. At the same concentration of the tested biological molecules, the intensity of the fluorescence signals in the experimental group is still 6174 a.u. while the magnetic beads are aggregated in the experimental group. In the subgroup where the magnetic beads are not aggregated in the control group, the lowest concentration of the tested biological molecules, which can be detected, is 10 pg/ml. In the subgroup where the magnetic beads are aggregated in the control group, the aggregation of the magnetic beads in the control group can only lower the detection limit to 1 pg/ml. In the experimental group, merely using the photonic crystal can lower the detection limit to $10^{-3}$ pg/ml. The cooperation of the photonic crystal and the magnetic beads can lower the detection limit to $10^{-4}$ pg/ml. In comparison with the detection limit 1 pg/ml of the subgroup using magnetic beads in the control group, the detection limit is $10^{-4}$ pg/ml, i.e. lowered by 4 order of magnitude, in the subgroup using magnetic beads in the experimental group. The experimental results prove that the integration of a photonic crystal magnetic beads and the magnetic bead-aggregation technology can significantly enhance the fluorescence signals by thousands of times and lower the detection limit to the scale of $10^{-4}$ pg/ml.

In conclusion, the present invention proposes a fluorescence immunoassay device and method based on the integration of a photonic crystal and magnetic beads, wherein the optical characteristics of the photonic crystal are used to increase the ability of exciting the fluorescent molecules and effectively direct the dispersive fluorescence signals to the fluorescence detector, and wherein the surface-to-volume ratio of the magnetic bead, which is higher than a planar carrier, is used to obtain a higher fluorescence density, whereby the detection limit of the tested biological molecules can be lowered to $10^{-4}$ pg/ml. Besides, the present invention also uses the aggregation of magnetic beads to further increase the fluorescence density and lower the detection limit of the tested biological molecules to $10^{-4}$ pg/ml. Therefore, the present invention can improve the insufficiency of the conventional immunoassay method in detection ability and is very suitable for the immunoassay of the biological molecules having an ultra-low concentration. The present invention is expected to apply to the fields of biology, chemistry, medicine, food industry, environmental protection, and agriculture.

The embodiments described above are only to exemplify the present invention but not to limit the scope of the present invention. Any equivalent modification or variation according to the characteristic or spirit of the present invention is to be also included by the present invention.

What is claimed is:

1. A fluorescence immunoassay device based on integration of a photonic crystal and magnetic beads, comprising
   a photonic crystal, said photonic crystal being a resonant waveguide grating structure;
   at least one magnetic bead disposed on a surface of said photonic crystal that is specific for a tested biological molecule;
   a plurality of the fluorescent molecules that are specific for the tested biological molecule;
   a light source providing an incident exciting light, wherein said incident exciting light resonates with said photonic crystal to enhance an electric field on said surface of said photonic crystal; said electric field further excites said fluorescent molecules to generate fluorescence signals intensified by said electric field; and
   a florescence detector receiving said fluorescence signals that said fluorescent molecules emit to said fluorescence detector and said fluorescence signals that are reflected from said photonic crystal, and processing said fluorescence signals into a sensed image.

2. The fluorescence immunoassay device based on integration of a photonic crystal and magnetic beads according to claim 1, wherein said tested biological molecules have a concentration of at least $10^{-3}$ pg/ml.

3. The fluorescence immunoassay device based on integration of a photonic crystal and magnetic beads according to claim 1, wherein said tested biological molecule is selected from a group consisting of nucleic acids, antigens, antibodies, binding proteins, phytohematoagglutinin, hormone receptors, and small-molecule compounds.

4. The fluorescence immunoassay device based on integration of a photonic crystal and magnetic beads according to claim 1 comprising a plurality of magnetic beads.

5. The fluorescence immunoassay device based on integration of a photonic crystal and magnetic beads according to claim 4 further comprising a magnetic device, wherein said magnetic device neighbors said magnetic beads and attracts said magnetic beads to aggregate on said surface of said photonic crystal.

6. The fluorescence immunoassay device based on integration of a photonic crystal and magnetic beads according to claim 5, wherein said tested biological molecules have a concentration of at least $10^{-4}$ pg/ml.

7. The fluorescence immunoassay device based on integration of a photonic crystal and magnetic beads according to claim 1, wherein said resonant waveguide grating structure includes a substrate, a grating layer and a waveguide layer; said grating layer is formed on said substrate; said waveguide layer is formed on said grating layer.

8. The fluorescence immunoassay device based on integration of a photonic crystal and magnetic beads according to claim 1, wherein said fluorescence detector detects a plurality of pixels of said sensed image and sets said pixels whose pixel values are smaller than a black balance value to be zero to eliminate noise of said sensed image.

9. The fluorescence immunoassay device based on integration of a photonic crystal and magnetic beads according to claim 1 further comprising an image processor, wherein said image processor receives said sensed image and analyzes intensities of said fluorescence signals according to said sensed image.

* * * * *